United States Patent [19]

Peerless et al.

[11] Patent Number: 5,137,523
[45] Date of Patent: Aug. 11, 1992

[54] OTOLOGICAL DRAIN TUBE

[76] Inventors: Sidney A. Peerless, 3131 Harvey Ave., Cincinnati, Ohio 45229; Joseph C. Burge, 1 Rabbits Run, Palm Beach Gardens, Fla. 33418

[21] Appl. No.: 712,473
[22] Filed: Jun. 10, 1991
[51] Int. Cl.$^5$ .............................. A61F 2/18
[52] U.S. Cl. .................. 604/264; 623/10; 604/8
[58] Field of Search ............ 604/8, 27, 30, 43, 45, 604/264, 266, 268; 623/10; 606/108, 109

[56] References Cited

U.S. PATENT DOCUMENTS

| | | | |
|---|---|---|---|
| 3,530,860 | 9/1970 | Ponce | 604/264 X |
| 3,807,409 | 4/1974 | Paparella et al. | 604/264 |
| 3,871,380 | 3/1975 | Heros | 604/264 |
| 3,916,873 | 11/1975 | Wasserman | 623/10 X |
| 3,976,081 | 8/1976 | Lapidot | 604/266 |
| 3,982,545 | 9/1976 | Silverstein | 604/264 |
| 4,094,303 | 6/1978 | Johnston | 623/10 X |
| 4,168,697 | 9/1979 | Cantekin | 604/264 X |
| 4,174,716 | 11/1979 | Treace | 604/264 |
| 4,695,275 | 9/1987 | Bruce et al. | 604/264 |
| 4,712,537 | 12/1987 | Pender | 604/14 X |
| 4,744,792 | 5/1988 | Sander et al. | 623/10 |
| 4,808,171 | 2/1989 | Berger | 604/264 |
| 4,964,850 | 10/1990 | Bouton et al. | 604/8 X |

FOREIGN PATENT DOCUMENTS 1362481 12/1987 U.S.S.R. .................. 604/264

Primary Examiner—Robert A. Hafer
Assistant Examiner—Sam Rimell
Attorney, Agent, or Firm—Jack N. McCarthy

[57] ABSTRACT

A drain tube for implanting in an ear drum is formed having a center body with a circular flange on each end with a cover member over each flange forming a chamber therewith. The cover members have openings therein and the center body has drain holes therethrough having a high L/D ratio to permit proper drain flow from an ear and prevent undesirable flow into an ear. A tab is used for insertion and a method of forming the drain holes is set forth wherein grooves are placed in the surface of a large opening and the grooves closed to form drain holes by a plug placed in the large opening.

11 Claims, 1 Drawing Sheet

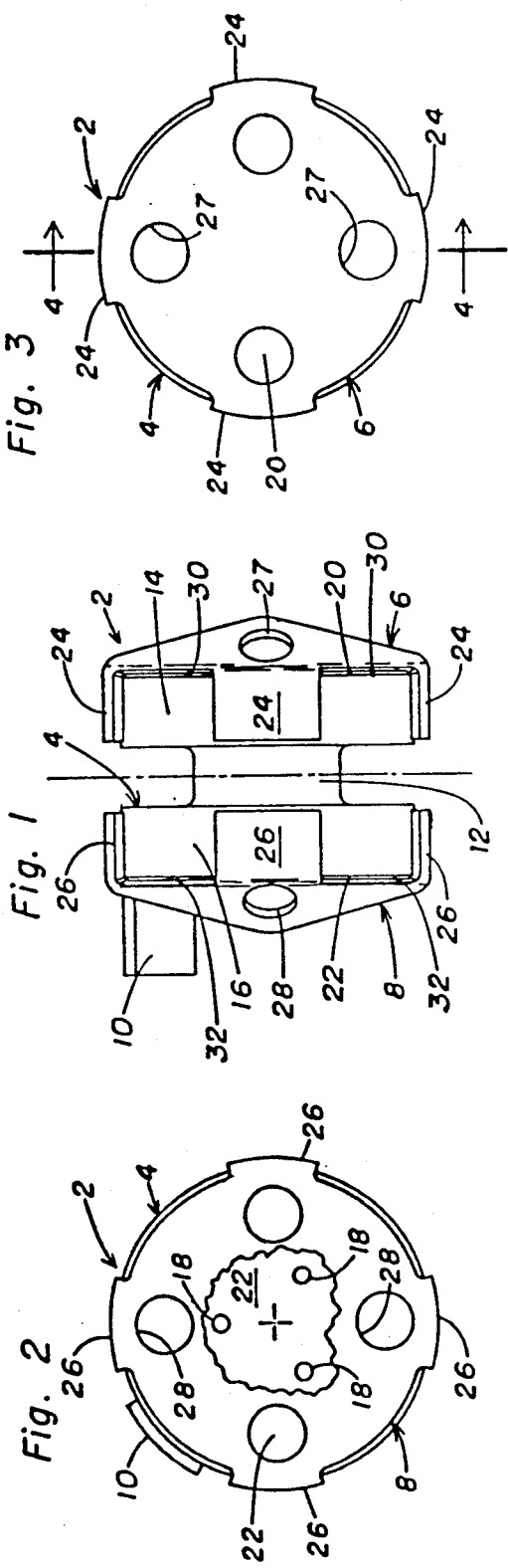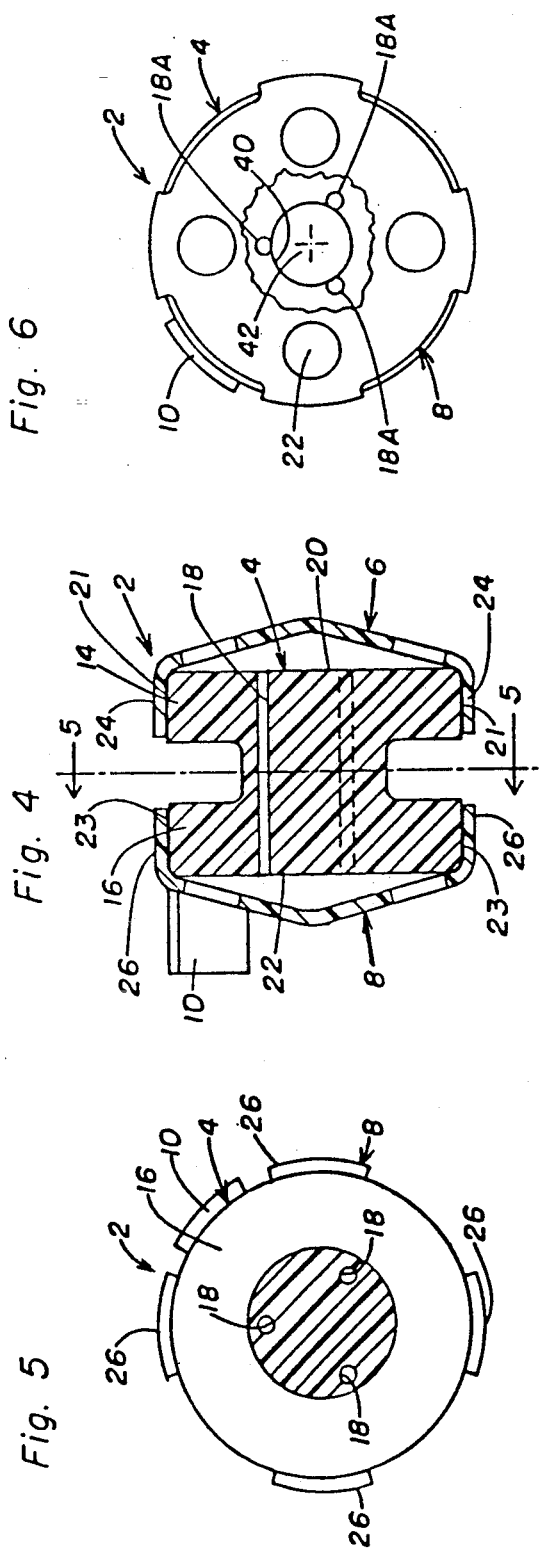

OTOLOGICAL DRAIN TUBE

DESCRIPTION

1. Technical Field

This invention relates to tubes for implanting in an ear drum to vent differential pressure build-up across the ear drum that can occur as a result of external ear pressure fluctuations or inner ear fluid pressures, including air pressure.

2. Description of the Prior Art

Drain tubes for the ear drum inserted into a hole through the ear drum have been used in the past. Patents showing prior art in this field are: U.S. Pat. Nos. 3,530,860; 3,807,409; 3,888,258; 3,897,786; 3,913,584; 3,948,271; 4,473,073; and 4,712,537.

DISCLOSURE OF THE INVENTION

It is an object of this invention to provide an otological drain tube which can fit within the confines of the ear drum locale.

It is another object of this invention to provide an otological drain tube which can be surgically sterilized; the otological drain tube material is acceptable for sterilization and the construction is formed to prevent cavities therein which would not have drain flow.

It is a further object of this invention to provide sufficient air flow capacity to vent the inner ear volume of an adult or child quickly during all normal activities. The primary purpose is to equalize the pressure of the middle ear with the external ear.

It is another object of this invention to minimize the flow of extraneous fluids into the inner ear during normal activities, such as bathing, or swimming.

It is a further object of this invention to also allow inner ear fluids to flow outward quickly enough to prevent patient discomfort.

It is another object of this invention to have any drain hole sized to have a high L/D ratio; that is, the ratio of the length of the hole over the diameter of the hole, such as 17.

BRIEF DESCRIPTION OF THE DRAWINGS

FIG. 1 is a side elevational view of the otological drain tube;

FIG. 2 is a view of the outer cover of the otological drain tube of FIG. 1;

FIG. 3 is a view of the inner cover of the otological drain tube of FIG. 1;

FIG. 4 is a view taken on the line 4—4 of FIG. 3;

FIG. 5 is a view taken on the line 5—5 of FIG. 4; and

FIG. 6 is a modified view of FIG. 2.

BEST MODE FOR CARRYING OUT THE INVENTION

Referring to FIG. 1, an otological drain tube 2 is shown having four main parts:

(1) a center body 4;
(2) an inner cover, or cap, member 6;
(3) an outer cover, or cap, member 8; and
(4) a holding tab 10.

The center body 4 is formed having a tubular mid-portion 12 with a spaced inner circular flange 14 at one end and an outer circular flange 16 at the other end. The inner circular flange 14 has an inner circular face 20 and a cylindrical end surface 21. The outer circular flange 16 has an outer circular face 22 and a cylindrical end surface 23. It is the center body 4 which provides the flow capacity of the otological drain tube 2.

The center body 4 is shown with three (3) drain holes 18 extending through the tubular mid-portion 12, inner circular flange 14, and outer circular flange 16. The ends of the drain holes 18 intersect the inner circular face 20 and outer circular face 22. However, the drain holes 18 have a sharp-edged inlet and exit at the circular faces 20, 22, and the holes 18 are roughened on their inner flow surface to control flow therethrough.

Inner cover member 6 is fixed over inner circular face 20 and outer cover member 8 is fixed over outer circular face 22. Inner cover member 6 is conical in shape with the base slightly smaller in diameter than the diameter of the inner circular face 20. Projecting flanges 24 extend from the outer periphery of the inner cover member 6 over the cylindrical end surface 21 of inner circular flange 14 and are fixed thereto. Four (4) such projecting flanges 24 are shown. Outer cover member 8 is conical in shape with the base slightly smaller in diameter than the diameter of the outer circular face 22. Projecting flanges 26 extend from the outer periphery of the outer cover member 8 over the cylindrical end surface 23 of outer circular flange 16 and are fixed thereto. The projecting flanges 24 and 26 can be fixed to the end surfaces 21 and 23, respectively, by any means desired, such as by spot welding.

The inner cover member 6 is positioned with its inner edge of the base spaced by a small distance from the inner circular face 20. This provides a narrow opening 30 therebetween. This narrow opening, or slit, 30 permits flow therethrough, preventing a collection of fluid. The outer cover member 8 is positioned with its inner edge of the base spaced by a small distance from the outer circular face 22. This provides a narrow opening 32, like narrow opening 30, therebetween.

The narrow openings, 30 and 32, insure that there is a gap between the inner and outer covers, or caps, 6 and 8, respectively, and the center body 4. These narrow openings, 30 and 32, are large enough to allow easy flushing of the drain tube 2 by antiseptic solutions, or other sterilizing means, but small enough to protect the drain holes 18 from foreign objects.

Inner and outer cover members 6 and 8 have four (4) openings each, 27 and 28, respectively, to permit flow of air and fluid to and from the drain holes 18. The openings 27 and 28 are offset axially from the otological drain holes 18 for debris protection.

After an incision is made in the ear drum, a long pointed instrument with a tip clamp is used to hold the tab 10 to insert the otological drain tube 2 through the confined space of the outer ear canal and into the ear drum incision. The tab 10 is fixed to the outer cylindrical surface of the outer circular flange 16, such as by welding. The tab 10 is the clamping point for the surgeon's instrument. The ear drum membrane, in a short time, grows around the otological drain tube 2, sealing the incision. Removal of the otological drain tube 2 is by the reverse process after separating the membrane from the drain tube 2.

In a design of an otological drain tube 2, three (3) drain holes 18 were made 0.005 inches in diameter, 0.085 inches in length, and placed on a 0.045 inch diameter circle. Drain holes 18 each have a sharp edge at both ends, the entrance and the exit, and have a roughened inner surface to restrict flow thereinto. The center body 4, inner and outer covers 6 and 8, and holding tab 10 were of stainless steel with no sharp edges on their outer surface. The openings 27 and 28 were made 0.025 inches in diameter. Each of these drain holes 18 had an L/D ratio of 17. This sizing permits the flow of fluid outwardly from the ear in any condition, and greatly reduces any undesirable flow into the ear. While one drain hole 0.005 inches in diameter will meet all of the necessary functioning requirements of the otological drain tube 2, three (3) drain holes of this size are provided to present a large margin of safety against potential clogging. A suggested range of L/D ratios is 8 to 26.

FIG. 6 is a modification where the center body 4 has a center opening 40 therethrough which has a center plug 42. This modification permits the formation of the drain holes 18A by an Electro Discharge Machining method without having a burning away of the material of the center body 4 around the drain hole 18A being formed. Incorporation of the center opening 40 gives an Electro Discharge Machining operator, or any other operator using a different method, open access from both ends of the otological drain tube 2 to form the drain holes 18A as open slots from inside the center opening 40. After the formation of the slots, the center plug 42 is fixed in place in the center opening 40 and the drain holes 18A are formed. In a design, the center opening 40 was to be 0.040 inches in diameter, and the grooves were to provide the desired L/D ratio when closed by the center plug 42.

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

We claim:

1. An otological drain tube having a center body, said center body having a tubular mid-portion with a circular flange on each end, a plurality of drain openings extending through said tubular mid-portion and said circular flanges, a first cover member fixed to one of said flanges, a second cover member fixed to the other of said flanges, opening means in each of said cover members.

2. A combination as set forth in claim 1 wherein one of said covers has a tapered shape to provide entry into an ear drum opening.

3. A combination as set forth in claim 1 wherein each of said circular flanges has an outer circular face, a first chamber is formed between the outer circular face of one of said circular flanges and said first cover member, a second chamber is formed between the outer circular face of the other of said circular flanges and said second cover member.

4. A combination as set forth in claim 1 wherein said first and second cover members have outer cylindrical edges, said first cover member having flanges extending from its outer cylindrical edge over the circular face of its cooperating circular flange and being fixed thereto, said opening means in each cover member entering into the chamber.

5. A combination as set forth in claim 1 wherein each drain opening has a large L/D ratio to permit proper drain flow from an ear and prevent undesirable flow into an ear.

6. A combination as set forth in claim 5 wherein the L/D ratio is in a range of 8 to 26.

7. A combination as set forth in claim 5 wherein the L/D ratio is 17.

8. A combination as set forth in claim 1 wherein said opening means in each of said cover means comprises a plurality of second openings, each of said second openings being offset from any drain opening so that no second opening will be aligned with a drain opening.

9. An otological drain tube having a center body, said center body having a tubular mid-portion with a circular flange on each end, a large opening extending through said tubular mid-portion and said circular flange on each end, a plurality of grooves placed along the surface of said large opening from one end to the other, a plug fixed in said large opening forming drain openings with said grooves, a first cover member fixed to one of said flanges, a second cover member fixed to the other of said flanges, opening means in each of said cover members.

10. A method of forming drain holes through an otological drain tube including the steps of:
   (1) forming the outer contour of an otological drain tube;
   (2) drilling a large opening through said otological drain tube;
   (3) forming grooves on the surface of said large opening;
   (4) placing a plug in said large opening to close said grooves and form drain holes.

11. A method as set forth in claim 10 wherein each of said grooves is formed of a predetermined size to form a proper L/D ratio drain hole when closed by the plug.

* * * * *